(12) United States Patent
Murnick (10) Patent No.: US 7,616,305 B2
(45) Date of Patent: Nov. 10, 2009

(54) ANALYTICAL METHODS AND APPARATUS

(75) Inventor: Daniel E. Murnick, Bernardsville, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 519 days.

(21) Appl. No.: 11/607,126

(22) Filed: Nov. 30, 2006

(65) Prior Publication Data

US 2008/0129994 A1    Jun. 5, 2008

(51) Int. Cl.
*G01J 3/30* (2006.01)
(52) U.S. Cl. ................................ 356/311
(58) Field of Classification Search ........... 356/311
See application file for complete search history.

(56) References Cited

U.S. PATENT DOCUMENTS

| | | | | | |
|---|---|---|---|---|---|
| 3,998,557 | A | * | 12/1976 | Javan | 356/434 |
| 4,402,606 | A | * | 9/1983 | Zalewski et al. | 356/315 |
| 5,394,236 | A | | 2/1995 | Murnick | |
| 5,689,334 | A | * | 11/1997 | Atkinson et al. | 356/326 |
| 5,706,082 | A | * | 1/1998 | Colgan et al. | 356/311 |
| 5,723,864 | A | * | 3/1998 | Atkinson et al. | 356/328 |
| 5,742,054 | A | * | 4/1998 | Atkinson | 250/339.13 |
| 5,783,445 | A | * | 7/1998 | Murnick | 356/311 |
| 5,818,580 | A | | 10/1998 | Murnick | |
| 6,064,488 | A | * | 5/2000 | Brand et al. | 356/440 |
| 6,800,855 | B1 | * | 10/2004 | Dong et al. | 250/339.13 |

OTHER PUBLICATIONS

Baev et al. "Laser intracavity absorption spectroscopy", Jul. 29, 1999, Applied Physics, B 69, pp. 171-202.*

McCarthy et al. "Low-Temperature Opto-Galvanic Spectroscopy without Discharges", 2003, Kluwer Academic Publishers, pp. 209-222.*

Murnick, D.E. et al., "Laser Based Carbon-14 Atom Counting For Biomedical Studies," Synthesis and Applications of Isotopies and Isotopically Labelled Compounds, vol. 8, 79-82, D.C. Dean, C.N. Filer and K.E. McCarty, eds., John Wiley & Sons, Chichester (2004.

Murnick, Daniel and Joseph O. Okil, "Use of the optigalvanic effect (OGE) for isotope ratio spectrometry of 13CO2 and 14CO2," Isotopes in Environmental and Health Studies, vol. 41, No. 4, Dec. 2005, pp. 363-371.

Murnick, D.E., et al., "LARA-An alternative to AMS and scintillation counting in Biomedical Studies, " 9th Int'l Symposiun on The Synthesis and Applications of Isotopes and Isotopically Labelled Compounds, Edinburgh Scotland, Abstract of talk presented Jul. 17, 2006.

Murnick, D.E. et al., "Laser based 14C counting, an alternative to AMS in biological sutdies," Nuclear Instruments and Methods in Physics Research B 259 (2007), pp. 786-789.

* cited by examiner

*Primary Examiner*—Kara E Geisel
(74) *Attorney, Agent, or Firm*—Lerner, David, Littenberg, Krumholz & Mentlik, LLP (57) ABSTRACT

A gaseous analyte including a small amount of a multiatomic moiety incorporating a particular isotope, such as $^{14}CO_2$ is subjected to a standing optical wave at a resonant wavelength of the moiety while maintaining the moiety in an excited condition, such as in a gas discharge. The standing optical wave may be applied by a laser having a sample cell containing the analyte within the laser cavity. Monitoring an induced effect such as the optogalvanic effect yields a signal directly related to the quantity of the moiety. The test can detect quantities of the moiety of an attomole or less, and in some cases on the order of 100 molecules.

25 Claims, 3 Drawing Sheets

ANALYTICAL METHODS AND APPARATUS

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. NIH 4 R33 RR018280 awarded by the National Institute Of Health.

FIELD OF THE INVENTION

The present invention relates to analytical methods and apparatus.

BACKGROUND OF THE INVENTION

In numerous analytical, scientific, and technical applications, it is necessary to determine the amount of an isotope in a material. Isotopes are different forms of the same chemical element, having atomic nuclei of different masses. For example, naturally occurring carbon consists predominantly of $^{12}C$, i.e., carbon having atomic mass of 12 atomic mass units with small amounts of $^{13}C$ and $^{14}C$ isotopes, having atomic masses of 13 and 14 atomic mass units respectively. For example, in medical testing and in drug development, it is a common practice to administer a drug or other substance to a living subject which has molecules incorporating $^{13}C$ or $^{14}C$ as a "tracer," and then measure the amount of $^{13}C$ or $^{14}C$ which appears in a particular tissue of the subject, or in substances exhaled or excreted by the subject. Where carbon is incorporated in a moiety such as small multi-atomic ion, radical, or molecule such as carbon dioxide ($CO_2$), moieties containing different isotopes of carbon will absorb and emit light at different wavelengths. This phenomenon is related to differences in the rotational and vibrational states of the multi-atomic moieties which arise from the different masses of carbon atoms.

Spectroscopy can be used to measure the amounts or relative concentrations of particular isotope-bearing moieties present in a sample. In conventional absorption spectroscopy, light at a wavelength corresponding to an absorption wavelength of a moiety containing a particular isotope is directed through a sample. The intensity of light after passage through the sample is measured and compared with the intensity of the applied light. However, conventional absorption spectroscopy requires a large sample containing a substantial concentration of the moiety to be measured. It is a relatively insensitive test.

As described, for example, in Baev, V. M., Latz, T., and Toshek, P. E., "Laser Intracavity Absorption Spectroscopy," App. Phys., V. 69(3), 171-202 (1999), it has been suggested that the sensitivity of absorption spectroscopy can be increased by placing the sample cell containing the sample inside of a laser. For example, a gas laser includes a tube filled with a gas disposed in a cavity between a pair of mirrors, one of which is a partially reflective mirror. When energy is applied to the gas, light emitted by the gas passes back and forth between the mirrors. As the light impinges on the medium, it stimulates emission of additional light which is coherent with the impinging light. A small portion of the light passing back and forth between the mirrors passes out of the laser through the partially reflective mirror. Thus, if the cell containing the sample is placed between the mirrors, it is exposed to each photon of light many times as the photon passes back and forth between the mirrors. Systems of this type are commonly referred to as "intracavity laser absorption spectroscopy" or "ICLAS". ICLAS typically is on the order of 100 times more sensitive than conventional absorption spectroscopy.

My own U.S. Pat. Nos. 5,394,236 and 5,818,580 describe techniques in which light is directed through a sample which includes multi-atomic moieties such as molecules or ions containing particular isotopes. The analyte typically is maintained in a condition such that at least some of the isotope-bearing moieties in the analyte are in excited states. For example, the analyte may be maintained in this condition by maintaining it as an ionized gas or plasma. At least some of the electrons in the molecules or ions are at energy levels higher than the energy levels occupied in the ground or normal state of the moieties. Such excited states have transition energies corresponding to the energy released upon transition from the excited state to a lower energy state, or absorbed upon the reverse transition, from the excited state to another, higher energy state. The transition energies are different for moieties incorporating different isotopes, as for example, $^{12}CO_2$, $^{13}CO_2$, and $^{14}CO_2$. Light at a wavelength corresponding to a transition energy of excited moieties including one isotope will interact with the moieties including that isotope, but will not substantially interact with moieties including the other isotopes. Light at the appropriate wavelength for each isotope to be monitored is applied to the sample, as by directing one or more beams from one or more lasers onto the sample and monitoring an induced effect, most commonly the optogalvanic effect. The optogalvanic effect refers to a change in the electrical impedance of a plasma. Methods according to the aforementioned patents provide considerable improvement over absorption spectroscopy. Methods according to these patents have been adopted, for example, in monitoring of environmental conditions and in certain medical testing procedures.

Murnick, D. E., Perez, M. A., and Polickal, M., "Laser Based $^{14}C$ Atom Counting For Biomedical Studies," Proceedings of the International Isotope Society Conference, June 2003, characterizes certain methods of this type as having a sensitivity "exceeding three picomoles of $^{14}CO_2$," i.e., as being capable of detecting quantities of $CO_2$ on the order of $3 \times 10^{-12}$ moles of $CO_2$. A "mole" is a quantity of a substance which contains $6.02 \times 10^{23}$ molecules or atoms, and which has a mass in grams equal to the atomic or molecular weight of the substance in atomic mass units ("AMU"). For example, a mole of $^{14}CO_2$ (total molecular weight 48 AMU) corresponds to 48 grams of $^{14}CO_2$. Thus, 3 picomoles is about $1.4 \times 10^{-10}$ grams of $CO_2$, i.e., about one tenth of 1 billionth ($10^{-9}$) of a gram. The same article notes that "a laser can be configured to incorporate a sample cell inside the laser cavity, which should yield a gain factor of 400 due to the circulating laser power," i.e., that an arrangement similar to that used in ICLAS can be employed with optogalvanic spectroscopy, and that "the proposed intracavity optogalvanic effect system should then yield sensitivity of order $10^{-10}$ to $10^{-11}$, and may provide even better results." A table in the same article states that such methods might be projected to have a sensitivity on the order of "$10^{-12}$ of better," i.e., one part $^{14}C$ in $10^{12}$ parts $^{12}C$ and $^{13}C$, using a sample size of 1 micromole. This corresponds to detection of $10^{-18}$ moles of $^{14}CO_2$, i.e., about $6 \times 10^5$ or 600,000 molecules of $^{14}CO_2$. While such a test is indeed sensitive, still further improvement would be desirable. For example, where a small dose of an isotopically-labelled drug is administered to a subject such as a human or animal, metabolic studies may require detection of the isotope at levels on the order of $10^{-20}$ moles (about 6000 molecules) of $^{14}CO_2$ or better, using a small sample size. Until the present invention, the only test method capable of achieving this level of sensitivity has been accelerator mass spectroscopy ("AMS"). Because AMS at this level of sensitivity requires a costly ion accelerator, it is a very expensive test method. Moreover, AMS suffers from other drawbacks.

SUMMARY OF THE INVENTION

One aspect of the present invention provides an analytical method including the steps of maintaining a gaseous analyte which includes less than about $10^{-18}$ moles of a multi-atomic moiety in a condition wherein the moiety is present in an excited state. The method according to this aspect of the invention desirably includes directing coherent light at a resonance wavelength of the moiety in the excited state along a path through the analyte so as to maintain a standing optical wave within the analyte. The method also most preferably includes the step of monitoring an induced effect such as the optogalvanic effect or other induced effects in the analyte, and determining the presence or amount of the moiety in the analyte based on the magnitude of the induced effect.

A method according to another aspect of the invention includes the step of operating a gas laser having a cavity between a pair of mirrors and having a lasing medium including a multi-atomic moiety, so as to produce coherent light at a wavelength corresponding to a transition energy of the moiety. A method according to this aspect of the invention desirably includes the step of maintaining an analyte including less than about $10^{-18}$ moles of the moiety in a condition wherein the moiety in the analyte is present in an excited state, and the analyte is disposed between the mirrors of the laser but separate from the lasing medium. In this condition, coherent light generated in the laser passes repeatedly through the analyte. A method according to this method of the invention desirably also includes the steps of monitoring an induced effect such as the optogalvanic effect in the analyte and determining the presence or amount of the moiety in the analyte based on the magnitude of the induced effect.

Preferred methods according to this aspect of the invention incorporate the discovery that the enhancement in sensitivity in optogalvanic spectroscopy and kindred processes using other induced effects achieved by the use of a standing wave, as for example, by the use of an intracavity arrangement, is many orders of magnitude greater than that which would have been expected, and which was projected in the aforementioned conference paper. Particularly preferred methods according to these aspects of the invention can detect quantities of material substantially smaller than $10^{-18}$ moles, and indeed can detect quantities on the order of 100 molecules, i.e., on the order of $10^{-21}$ to $10^{-22}$ moles of material. Inter alia, preferred methods according to these aspects of the invention can provide exquisitely sensitive and accurate tests for isotopically-labelled $CO_2$ and other multi-atomic species.

DETAILED DESCRIPTION

Apparatus for use in a method according to one embodiment of the invention (FIG. 1) includes a laser 10 incorporating a gas tube 12 containing a gas mixture which includes a multi-atomic moiety corresponding to the moiety to be measured, referred to herein as the "moiety of interest". In the embodiment discussed, the moiety of interest is $^{14}C^{16}O_2$, i.e., carbon dioxide molecules formed from the rare carbon isotope $^{14}C$ and ordinary oxygen which is predominantly $^{16}O$. Unless otherwise specified, the expression "$^{14}CO_2$" should be understood as referring to $^{14}C^{16}O_2$. The moiety of interest constitutes the lasing moiety in the gas mixture, i.e., the moiety which undergoes a transition between states to produce the laser emission. As is conventional in gas lasers, the lasing moiety may be provided in a mixture with other gaseous components. In the case of $^{14}CO_2$, the lasing moiety desirably is provided in a mixture with nitrogen, and may also include helium and xenon. For example, the gas mixture may contain about 60% He, 20% $N_2$, 15% $CO_2$ and 5% Xe. Laser tube 12 is formed from a material which is transparent to light at a transition wavelength of the lasing moiety, and is provided with Brewster windows 13 at its ends, i.e., windows set at an angle to the longitudinal axis 15 of the laser equal to the Brewster angle to suppress reflection of light passing along the axis 15. Laser 10 also includes a pair of mirrors 16 and 18. Mirror 16 desirably is fully reflective, whereas mirror 18 desirably is partially reflective. These mirrors are disposed on the axis 15 of the laser and define a cavity between the mirrors. In the conventional manner for a gas laser, the distance between the mirrors is selected so that it is equal to an integral number of wavelengths of the light emitted by the lasing moiety in tube 12. As is also conventional in gas laser practice, a source of excitation energy is associated with laser tube 12. In the embodiment depicted, the excitation source includes a power source 20 connected to electrodes 22 associated with laser tube 12 for maintaining a DC discharge within the laser tube. In other embodiments, the power source may be an RF generator connected to a coil associated with the laser tube.

Figure 1:
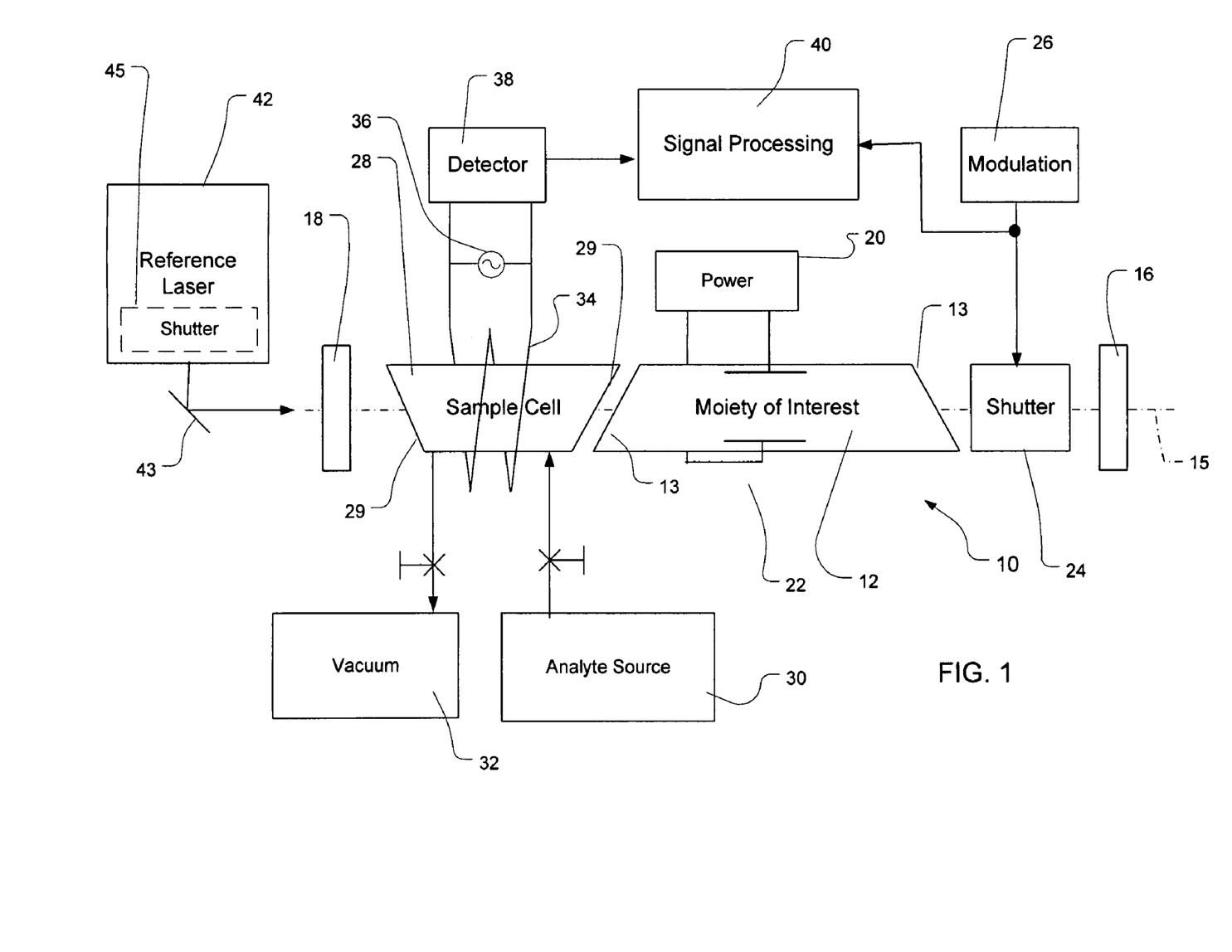
FIG. 1 is a functional block diagram of apparatus according to one embodiment of the invention.

A shutter 24 is also disposed in the laser cavity between mirrors 16 and 18. Shutter 24 is electrically controllable to transmit or block propagation of light along axis 15 within the laser cavity. Shutter 24 is connected to a modulation driver 26. The modulation driver provides a signal at a preselected frequency, desirably on the order of a few Hz or tens of Hz to the shutter so as to open and close the shutter at this frequency.

A sample cell 28 is also disposed within the laser cavity, between mirrors 16 and 18 on axis 15. The sample cell is a hollow chamber formed from a dielectric material, and has transparent Brewster windows 29, again disposed at the Brewster angle relative to the axis 15. The sample cell is connected to a source 30 of a gaseous analyte and to a vacuum source 32. Appropriate connections (not shown) may be provided for connecting the sample cell to a source of a purge gas. The apparatus may have any dimensions. However, good results can be achieved with a relatively small sample cell as, for example, a tubular sample cell having a length less than 1 meter and desirably less than 10 cm. [inventor please check]. The remainder of the apparatus also may be compact. For example, laser tube 12 may be less than 1 meter long, and the entire instrument may occupy about 1 m³ or less. Indeed, the entire instrument may be arranged to fit on a laboratory bench top.

An RF coil 34 surrounds sample cell 28. Coil 34 is connected to an RF generator 36 arranged to apply an RF signal through the coil. Coil 34 is also connected to a detector 38 arranged to detect the current passing through the coil and the voltage applied to the coil, and to provide a signal representing the impedance of the coil, and thus also representing the electrical impedance of a gas discharge within sample cell 28. A signal processing unit 40 is connected to receive the impedance signal from detector 38, and to receive the modulation signal applied to shutter 24 by modulation driver 26. The signal processing unit 40 is arranged to filter the impedance signal from detector 38 so as to select isolate a component in the impedance signal which varies in synchronism with the modulation signal from driver 26, and desirably, to average that component of the impedance signal over numerous cycles of the modulation signal so as to provide a time-averaged impedance signal. As discussed below, that time-averaged impedance signal will represent the optogalvanic response of the gas sample within sample cell 28. Detector 38, signal processing unit 40, and modulation driver 26 may be implemented using conventional components. For example, detector 38 typically includes amplifiers and digitizers, and signal processing unit 40 typically includes elements of a general-purpose computer. Modulation driver 26 may be controlled by the same computer and may be arranged to apply the modulation signal as a square wave, i.e., an on/off signal, to shutter 24.

The apparatus also includes a reference laser 42. Reference laser 42 desirably is a gas laser which includes a moiety corresponding to the moiety of interest used in laser tube 12 but having a different isotopic composition. For example, where the moiety of interest as used in laser tube 12 is carbon dioxide of one isotopic combination such as $^{14}CO_2$, the lasing moiety in the reference laser may be carbon dioxide of another isotropic combination such as $^{12}CO_2$. Reference laser 42 desirably includes a shutter 45 or other modulation apparatus which can be controlled by modulation generator 26. Reference laser 42 is arranged to direct a beam into sample cell 28 along axis 15, as for example, by directing the beam to one or more redirecting mirrors 43 and then through partially reflective mirror 18.

A method according to one embodiment of the invention utilizes $^{14}CO_2$ as the moiety of interest. As mentioned above, laser tube 12 of gas laser 10 contains a mixture including $^{14}CO_2$ in a mixture with nitrogen. An analyte in source 30 includes an unknown small amount of $^{14}CO_2$ along with substantially larger amounts of $^{12}CO_2$, $^{13}CO_2$, or both. The analyte desirably also includes nitrogen, and may include nitrogen in together with oxygen, as for example, about 80% nitrogen and about 15% oxygen by volume. For example, the sample may include air in admixture with the $CO_2$ component. The $CO_2$ (of all isotopic compositions) desirably constitute about 5% or less by mole fraction of the analyte. Also, where the moiety of interest is a $CO_2$ molecule and the measurement uses the optogalvanic effect, the analyte most desirably is essentially free of helium. Helium tends to inhibit the optogalvanic effect. Gas laser 10 is operated at a transition wavelength of the moiety of interest or $^{14}CO_2$, which differs substantially from transition wavelengths of other $CO_2$ species. For example, a wavelength of 11.768 microns may be used. Mirrors 16 and 18 are adjusted so that they are spaced from one another by an integral number of wavelengths, and power source 20 is actuated to produce a gas discharge within tube 12. Modulation source 26 is operated to open and close shutter 24 at a preselected modulation or chopping frequency.

Under these conditions, while shutter 24 in the open condition, the laser produces coherent light at the selected wavelength propagating along axis 15. In the conventional manner, the light passes repeatedly between mirrors 16 and 18, with a small proportion of the light exiting through mirror 18. The laser desirably has output power (delivered through mirror 18) on the order of a watt to a few watts, and internal optical power on the order of about 10-100 watts as, for example, about 50 watts. Stated another way, each photon emitted by the gas mixture in tube 12 will pass back and forth repeatedly between mirrors 16 and 18. A standing optical wave exists between mirrors 16 and 18. Of course, when shutter 24 is in the closed condition, no light propagates along axis 15.

A sample gas from analyte source 30 is admitted to sample cell 28, and sample cell 28 is maintained under a subatmospheric pressure, desirably below about 100 milibars and most preferably about 5-10 milibars. RF source 36 is operated to produce a low-power electrical discharge within sample cell 28. Typically, about 1-10 watts and most preferably about 2-5 watts of RF power is applied by source 36. Thus, the gaseous sample within sample cell 28 is maintained in the form of a glow type plasma. Under these conditions, a substantial proportion of the gaseous moieties in the sample, and particularly a substantial proportion of the $^{14}CO_2$ molecules in the sample, are present in excited states, with one or more electrons above their normal or ground states. The light passing back and forth along axis 15 interacts with the $^{14}CO_2$ moieties. Such interaction includes both optical absorption or promotion of moieties to a higher-energy state, and stimulated emission, i.e., triggering of decay from the excited state to a lower-energy state. These interactions alter the electrical impedance of the gas in the discharge. This causes the signal from detector 38 to vary. The component of the detector signal which varies in synchronism with the opening and closing of shutter 24 and hence in synchronism with modulation signal 26, is the signal component caused by the optogalvanic effect within sample cell 28. This signal component, referred to hereinafter as the analyte signal or $S_{analyte}$ is substantially proportional to the $^{14}CO_2$ concentration within the sample chamber and hence the amount of $^{14}CO_2$ present in the sample.

According to the conventional principles of optogalvanic spectroscopy, if a laser of intensity I and wavelength λ is incident on a cylindrical (length L and radius R), weak electrical discharge, the electrical response, S, of the discharge can be expressed by an integral over the laser-discharge interaction volume:

$$S = \int_0^L dz \int_0^R r\, dr \int_0^{2\pi} d\theta [n(r,\theta) I(r,\theta,z,v)\sigma(\lambda)K] \quad (1)$$

In this formula, the density of the interacting moiety is n, whereas σ(λ) represents the interaction cross section between the light at wavelength λ. S can be any discharge parameter related to conductivity, including $S_{analyte}$ and K is a corresponding optogalvanic proportionality constant that depends on the details of the electrical discharge. To a very good approximation, where λ is a wavelength corresponding to a resonance wavelength of the interacting moiety, and where light absorption in the sample cell is small in comparison to the average laser intensity, the average electrical response simplifies to a product:

$$S = nLIA\sigma K \quad (2)$$

In formula (2), n represents the average molecular density of the interacting moiety, L is the length of the interaction region, I the average laser intensity in W/cm², and A the average area of the laser beam.

As mentioned above, within laser 10, the light passes repeatedly between the two mirrors 16 and 18. On average, each photon is reflected repeatedly so as to pass through the sample cell Q times. Thus, in equation (2), the interaction length L is equal to $QL_p$, where $L_p$ is the physical length of the sample cell along the axis 15 of the laser. Accordingly, the optogalvanic signal S predicted by conventional theory for a system with the sample cell positioned inside the laser is:

$$S = nQL_p I A \sigma K \quad (3)$$

The intensity I as referred to in formula (3) is the intensity of the beam propagating internally within laser 10, between the mirrors 16 and 18. This intensity typically is greater than the intensity of the beam passing out of the laser through the output coupler or partially-reflective mirror 18. The signal magnitude calculated according to formula (3) is referred to herein as the expected signal magnitude based on the length of the signal path.

In a typical system, the expected signal magnitude based on the length of the path typically is about 10-400, most commonly about 100, times the signal magnitude which would be observed in an identical system having sample cell 28 disposed outside of laser 10, so that the light passes through the sample cell only once.

In practice, however, the magnitude of the optogalvanic signal $S_{analyte}$ is many times greater than the expected signal magnitude based on the length of the signal path as calculated according to formula (3). In practice, the observed signal typically is on the order of a million to 10 million times stronger than that which would be observed in an identical system having sample cell 28 disposed outside of the laser 10 so that the light passes through the sample cell only once. Stated another way, the observed optogalvanic signal typically is more than 100 times the expected signal magnitude based on the length of the path, and most commonly more than 1,000 times the expected signal magnitude based on the length of the path.

This surprising result is believed to be due to the presence of a standing optical wave within the laser cavity, between mirrors 16 and 18. In the case of a standing optical wave, it is believed that the effective value for the path length L in formula (2) is not simply $QL_p$ as discussed above, but in fact, is given by $C(\Delta T)$, where C is the speed of light and $\Delta T$ is an interaction time apparently related to the coherence time of the gas laser. Regardless of the underlying theory of operation, however, it has been found that operation of the optogalvanic cell within a standing wave gives dramatically and unexpectedly stronger optogalvanic response, and that this phenomenon occurs in those cases where such an enhanced response is most needed, i.e., in samples having extremely small amounts of the moiety of interest. Based upon conventional theory, the lower limit for detection of $^{14}CO_2$ is expected to be about 1 attomole, i.e., $10^{-18}$ moles of $CO_2$ within sample chamber 28, or about 600,000 molecules of $CO_2$ in the sample chamber. However, as discussed further below, the system can detect amounts of $^{14}CO_2$ as small as 100 molecules or less.

The optogalvanic signal $S_{analyte}$ observed during operation with the sample arises principally from interaction between the laser beam and the $^{14}CO_2$ in the analyte. However, there is a very weak non-resonant interaction between the laser beam at the resonant wavelength associated with the moiety of interest and other moieties present in the sample. These non-resonant interactions can produce some portion of the optogalvanic signal $S_{analyte}$. For example, where $^{14}CO_2$ is the moiety of interest and light at the 11.768 μm resonant wavelength of $^{14}CO_2$ is used, there is a very weak non-resonant interaction with $^{13}CO_2$. The interaction cross-section $\sigma(\lambda)$ between light at 11.768 μm and $^{13}CO_2$ is on the order of 10 orders of magnitude smaller than the interaction cross section between light at the same wavelength and $^{14}CO_2$. However, where the concentration of the moiety of interest is very small in comparison to the concentration of other moieties which have such non-resonant interactions, the signal due to the non-resonant interactions can constitute a significant portion of $S_{analyte}$. To compensate for this effect, the steps discussed above may be repeated using a blank sample in place of the analyte. The blank sample has the same composition but has zero concentration of the moiety of interest. All other conditions (including the pressure within the sample chamber 28 and the magnitude of the RF signals applied by sources 20 and 36) should be the same as those used for the analyte. The resulting optogalvanic signal $S_{blank}$ is subtracted from $S_{analyte}$ to yield a corrected analyte optogalvanic signal $S_{corr}$. $S_{corr}$ is directly proportional to the concentration of the moiety of interest in the analyte. In the particular case of a $^{14}CO_2$ moiety of interest, it has been found that the effect of non-resonant interactions of $^{13}CO_2$ is so small that it does not appreciably influence $S_{analyte}$, and therefore the blank sample correction is not necessary.

In a further step of the method, the reference laser 42 is actuated to apply light at a resonant wavelength associated with a reference moiety having the same chemical composition as the moiety of interest but having a different isotopic composition while the analyte is present in sample cell 28. Where the moiety of interest is $^{14}CO_2$, the reference laser is operated at a resonant wavelength associated with $^{12}CO_2$ or $^{13}CO_2$. The light intensity from reference laser 42 is also modulated at the modulation or chopping frequency set by modulation generator 26. The light from the reference laser passes through mirror 18 and passes once through sample chamber 28. During this step, the RF generator 36 and detector 38 are actuated in the same manner as discussed above. The light from the reference laser interacts with the reference moiety to yield an optogalvanic signal due to resonant interaction between the light from the reference laser and the reference moiety in the sample. Because the concentration of the reference moiety in the sample is many times greater than the concentration of the moiety of interest, the optogalvanic signal generated in this stage will have a substantial magnitude even though the beam from the reference laser only passes through the sample once. This optogalvanic signal will also vary at the modulation frequency. In the same manner as discussed above, the signal processor 40 filters the signal from detector 38 to select the signal component varying at the modulation frequency, and averages that signal component over numerous modulation cycles to provide a processed reference optogalvanic signal. This signal $S_{reference}$ can be used as a normalization signal. The normalized signal or ratio $S_{corr}/S_{reference}$ is proportional to the ratio between the concentration of the moiety of interest and the concentration of the reference moiety in the analyte. Stated another way, where the moiety of interest and the reference moiety have the same chemical composition but include different isotopes, the normalized signal or ratio is directly proportional to the isotopic concentration ratio in the sample. The normalized ratio is independent of factors related to the particular instrument such as the physical length Lp of the sample cell, the configuration of the RF coil 34, and the like. The normalized signal obtained using an unknown sample can be compared directly to a calibration curve of the normalized signals obtained using samples having known concentrations of the moiety of interest to derive a numerical value for concentration of the moiety of interest in the unknown sample.

The foregoing techniques can be applied with a wide range of moieties as the moiety of interest. In general, any multiatomic molecule, radical or ion may be employed. However, small moieties containing less than about 5 atoms are preferred. Carbon dioxide molecules are particularly useful because $CO_2$ molecules having different isotopic compositions tend to have widely-separated transition wavelengths. Moreover, essentially any carbon-containing substance can be converted readily to $CO_2$. $^{14}CO_2$ is particularly preferred because the level of $^{14}C$ in the environment is very small, on the order of one part per trillion (ppt). Stated another way, the ratio of $^{14}C$ to $^{12}C$ is on the order of $10^{-12}$, so that there is very little interference from naturally-occurring $^{14}C$. $^{14}C$ is relatively rare because, unlike other carbon isotopes, $^{14}C$ is radioactive and decays to form other atoms. However, the rate of such radioactive decay is extremely slow; the half-life of $^{14}C$ is 5730 years. Thus, the effects of radioactive decay during a the time of a typical measurement do not appreciably influence the results. Stated another way, $^{14}C$ can be considered as a stable isotope in typical measurements using the present invention. Other variants of $CO_2$, labeled with isotopes of oxygen can be used as the moiety of interest as, for example, $^{12}C^{18}O_2$ or $^{12}C^{18}O^{16}O$.

The method optionally may include the step of deriving the analyte from a sample of a biological material. For example, where a $^{14}C$-labelled substance is administered to a living organism or to living cells or tissues, the analyte may be derived from the organism, cells or tissues, or from substances exhaled or excreted by the organism. The step of deriving the sample may include essentially any conventional procedure capable of isolating the substance of interest as, for example, such as gas or liquid chromatography and separation procedures based on binding of biologically-derived molecules such as nucleic acids and proteins to particular biological substrates. The carbon in the isolated biological substance can be converted to $CO_2$ by oxidation. Only a small amount, on the order of a few micrograms or less, and typically one microgram or less of carbon is required.

In the foregoing discussion, the optogalvanic effect is monitored. However, induced effects other than the optogalvanic effect can be monitored. As used in this disclosure, the term "induced effect" means a phenomenon other than the change in radiation intensity at the applied wavelength during application of the radiation. In addition to the optogalvanic effect, induced effects include acoustical energy generation by the applied light referred to as the opto-acoustic effect; and stimulated fluorescence, or emission of light at a wavelength other than the applied wavelength or at a time other than the time of application of the light.

In the apparatus depicted in FIG. 1, the sample cell is disposed within the laser cavity, and thus is exposed to the standing optical wave which is inherently present during lasing. Other arrangements which produce a standing optical wave can be employed. For example, a standing optical wave can be maintained between a pair of mirrors including a partially-reflective mirror by directing a laser beam into the cavity between the mirrors from outside of the cavity. Also, an ideal standing optical wave has nodes and antinodes which remain perfectly stationary during the presence of the standing wave. However, the term "standing optical wave" as used herein should be understood as also including those waves which have nodes and antinodes which move slowly in comparison to the speed of light in the medium. Stated another way, in an ideal standing optical wave, the photon density at any location remains constant for an infinite time. However, the term "standing wave" as used herein should be understood as including waves in which the photon density at any point remains substantially constant over a time on the order of microseconds or milliseconds. Where the optical wave is modulated as in the embodiment discussed above, a wave in which the photon density at any point remains substantially constant over a time equal to the cycle time of the modulation can be considered a standing wave. Although the present invention is not limited by any theory of operation, it is believed that the reason why the standing wave provides enhanced results arises from the presence of constant photon density at points within the analyte. Other methods of providing a constant photon density, which do not involve the use of a standing wave, can be used.

In a further variant, the reference laser 42 of FIG. 1 is omitted and replaced by an additional laser tube containing a reference moiety such as $^{12}CO_2$ disposed in the cavity between mirrors 16 and 18. In yet another variant, tube 12 may contain both the moiety of interest and the reference moiety, so that the same laser can be operated either at the transition energy of the moiety of interest or the transition energy of the reference moiety. In yet another variant, no reference moiety is employed.

In the apparatus of FIG. 1, the detector monitors the optogalvanic effect by monitoring the signal in the RF coil 34. Other structures can be used for monitoring the optogalvanic effect as, for example, electrodes disposed within the sample chamber. Still other detectors, such as photodetectors and acoustical detectors, can be used to monitor other induced effects and provide a signal representing such other effects.

The following non-limiting examples illustrate certain features of the invention:

Example 1

Figure 2:
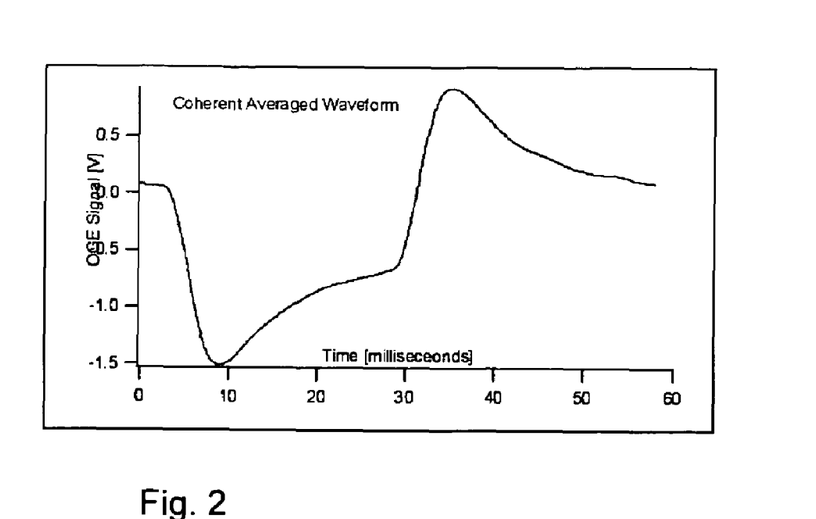
FIGS. 2, 3, and 4 are graphs depicting observations during processes according to certain embodiments of the invention.

A sample of 95% $N_2$, 5% $CO_2$ by mole fraction incorporating 0.15 micro moles $CO_2$ of which 1.5 attomoles is $^{14}CO_2$ was tested in an apparatus substantially as shown in FIG. 1. The laser is modulated at 17 Hz and operated at a wavelength of 11.768 µm. The optogalvanic signal $S_{analyte}$ was averaged coherently with the modulation over three seconds (51 modulation cycles) to yield a coherent average waveform as shown in FIG. 2.

Example 2

Figure 3:
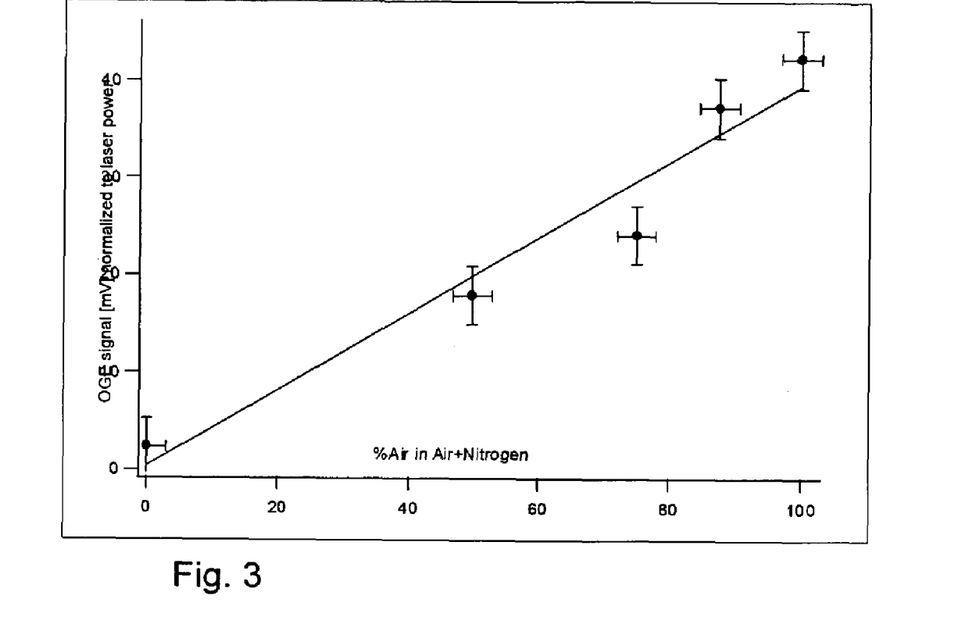
Figure 4:
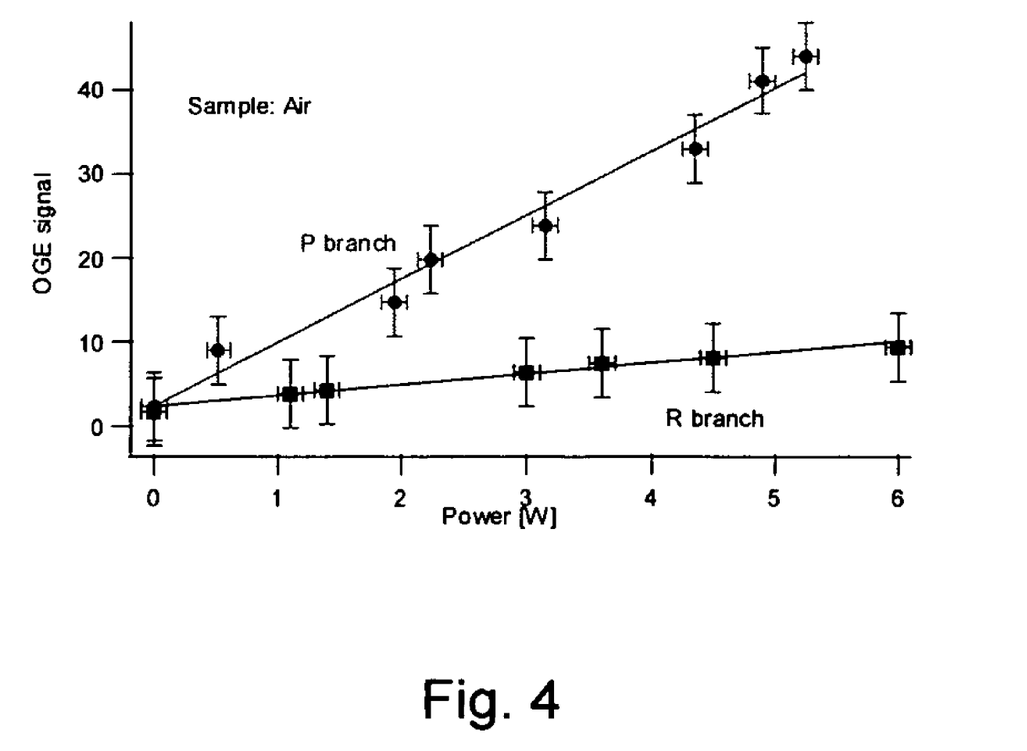

Ambient atmospheric air contains about 0.03% $CO_2$, of which about 1 part in $10^{12}$ is $^{14}CO_2$. A series of analytes was made by diluting the room air with pure nitrogen. The analytes were tested using conditions substantially as in Example 1. The laser power applied differed for various samples. To permit comparison between the various samples, the magnitude of the optogalvanic signal $S_{analyte}$ was normalized to the applied laser power. A graph of the normalized optogalvanic signal versus percent air is shown in FIG. 3. These results indicate that the system is capable of detecting on the order of 100 $^{14}C$ atoms in an air sample containing only 10 ng total carbon.

Example 3

A sample of ambient atmospheric air is tested in apparatus substantially as in Example 1, with varying levels of laser power at two different resonant wavelengths of $^{14}CO_2$: 11.768 µm corresponding to the P20 branch or "P branch", and 11.344 µm corresponding to the R20 branch or "R branch." The optogalvanic signal $S_{analyte}$ is plotted against laser output power. In this apparatus, the internal laser power is about 6.7 times the output power. These results indicate that the optogalvanic effect does not saturate at the power levels employed. These results also demonstrate that either wavelength can be used to provide a useful optogalvanic signal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An analytical method comprising the steps of:
   (a) maintaining a gaseous analyte including a multi-atomic moiety in a condition wherein the moiety is present in an excited state;
   (b) directing coherent light at a resonance wavelength of the moiety in the excited state along a path through the analyte so as to maintain a substantially constant photon density at locations along the path within the analyte;
   (c) monitoring an induced effect in the analyte having a magnitude at least ten times greater than a magnitude expected based on the length of the path; and
   (d) determining at least one the presence or amount of the moiety in the analyte based on the magnitude of the induced effect.

2. A method as claimed in claim 1 wherein said step of directing coherent light is performed so as to maintain a standing optical wave within the analyte.

3. An analytical method comprising the steps of:
   (a) maintaining a gaseous analyte including less than about $10^{-18}$ moles of a multi-atomic moiety in a condition wherein the moiety is present in an excited state;
   (b) directing coherent light at a resonance wavelength of the moiety in the excited state along a path through the analyte so as to maintain a standing optical wave within the analyte;
   (c) monitoring an induced effect in the analyte; and
   (d) determining at least one of the presence or amount of the moiety in the analyte based on the magnitude of the induced effect.

4. An analytical method comprising the steps of:
   (a) generating coherent light at a resonance wavelength of a multi-atomic moiety in a laser;
   (b) maintaining a gaseous analyte including a multi-atomic moiety within a chamber outside of the laser in a condition wherein the moiety is present in an excited state;
   (c) directing coherent light from the laser into the chamber so as to maintain a standing optical wave within the analyte;
   (d) monitoring an induced effect in the analyte; and
   (e) determining at least one the presence or amount of the moiety in the analyte based on the magnitude of the induced effect.

5. An analytical method comprising the steps of:
   (a) operating a gas laser having a cavity between a pair of mirrors and a lasing medium including a multi-atomic moiety to produce coherent light at a wavelength corresponding to a transition energy of the moiety;
   (b) maintaining an analyte including less than about $10^{-18}$ moles of the moiety in a condition wherein the moiety in the analyte is present in an excited state between the mirrors but separate from the lasing medium so that coherent light generated in said laser passes through the analyte;
   (c) monitoring an induced effect in the analyte; and
   (d) determining at least one of the presence or amount of the moiety in the analyte based on the magnitude of the induced effect.

6. A method as claimed in claim 1 or claim 5 wherein the step of maintaining the analyte includes maintaining the analyte in an electrical discharge.

7. A method as claimed in claim 1 or claim 5 wherein the moiety is selected from the group consisting of molecules, free radicals and ions having 5 atoms or less.

8. A method as claimed in claim 7 wherein the moiety is selected from the group consisting of molecules, free radicals and ions having 3 atoms or less.

9. A method as claimed in claim 7 wherein the moiety is carbon dioxide of a particular isotopic composition.

10. A method as claimed in claim 9 wherein the moiety is $^{14}C^{16}O_2$.

11. A method as claimed in claim 9 wherein the analyte includes nitrogen and oxygen.

12. A method as claimed in claim 9 wherein the analyte includes air.

13. A method as claimed in claim 9 wherein the analyte is essentially free of helium.

14. A method as claimed in claim 1 or claim 5 wherein the analyte includes less than about $10^{-19}$ moles of the moiety.

15. A method as claimed in claim 14 wherein the analyte includes less than about $10^{-20}$ moles of the moiety.

16. A method as claimed in claim 1 or claim 5 wherein the moiety is multiatomic chemical species including a first isotope and wherein the analyte further includes said multiatomic chemical species including a second isotope different from said first isotope.

17. A method as claimed in claim 16 wherein a concentration of said first isotope in the said multiatomic chemical species is about 1 part in $10^{10}$ or less.

18. A method as claimed in claim 1 or claim 5 wherein said monitoring step includes monitoring the magnitude of the induced effect and the determining step includes determining an amount of the moiety in the analyte based at least in part on said magnitude.

19. A method as claimed in claim 18 further comprising repeating the aforesaid steps with a blank sample of the same composition as the analyte but devoid of the moiety and monitoring the magnitude of an induced effect for the blank sample, the step of determining an amount of the moiety including subtracting the magnitude of the induced effect for the blank sample from the magnitude of the induced effect for the analyte.

20. A method as claimed in claim 1 or claim 5 wherein the step of monitoring the induced effect is performed by monitoring the optogalvanic effect.

21. A method as claimed in claim 1 or claim 5 further comprising the step of modulating the amplitude of the coherent light, the step of monitoring an induced effect being performed in synchronism with the amplitude modulation.

22. Apparatus for determining the presence or amount of a moiety in an analyte comprising:
   (a) a sample cell containing a gaseous analyte including less than about $10^{-18}$ moles of a multi-atomic moiety;
   (b) an energy application associated with the sample cell for maintaining the analyte in a condition wherein the moiety is present in an excited state;
   (c) a source of coherent light at a resonance wavelength of the moiety in the excited state arranged to direct the coherent light along a path through the sample cell so as to maintain a standing optical wave within the analyte; and (d) a detector for monitoring an induced effect in the analyte and providing a signal representing the induced effect.

23. Apparatus as claimed in claim 22 further comprising a modulator for modulating the coherent light at a modulation frequency.

24. Apparatus as claimed in claim 23 further comprising a signal processor for filtering the signal to isolate a component at the modulation frequency.

25. Apparatus as claimed in claim 22 wherein the detector is arranged to monitor the optogalvanic effect.

* * * * *

UNITED STATES PATENT AND TRADEMARK OFFICE
CERTIFICATE OF CORRECTION

PATENT NO. : 7,616,305 B2  Page 1 of 1
APPLICATION NO. : 11/607126
DATED : November 10, 2009
INVENTOR(S) : Daniel E. Murnick It is certified that error appears in the above-identified patent and that said Letters Patent is hereby corrected as shown below:

Column 2, line 47, "3 picomoles is" should read -- 3 picomoles are --.
Column 2, line 55, "of order $10^{-10}$" should read -- on the order of $10^{-10}$ --.
Column 2, line 58, "of better" should read -- or better --.
Column 4, line 53, delete the phrase "[inventor please check]" in its entirety.
Column 4, line 64, "representing" should read -- represent --.
Column 5, lines 43-44, "constitute" should read -- constitutes --.
Column 11, line 18, "one the" should read -- one of the --.
Column 11, line 47, "one the" should read -- one of the --.
Column 12, line 25, "multiatomic" should read -- a multi-atomic --.
Column 12, line 31, "multiatomic" should read -- multi-atomic --.

Signed and Sealed this

Fourteenth Day of December, 2010

David J. Kappos
*Director of the United States Patent and Trademark Office*